(12) United States Patent
Fattaccioli et al.

(10) Patent No.: US 12,269,000 B2
(45) Date of Patent: Apr. 8, 2025

(54) COLLOIDAL PARTICLES FUNCTIONALIZED HOMOGENEOUSLY BY BIOMOLECULES

(71) Applicants: Paris Sciences et Lettres, Paris (FR); Centre National de la Recherche Scientifique (CNRS), Paris (FR); Sorbonne Universite, Paris (FR)

(72) Inventors: Jacques Fattaccioli, Paris (FR); Lea Pinon, Vincennes (FR); Lorraine Montel, Cachen (FR)

(73) Assignees: Paris Sciences et Lettres, Paris (FR); Centre National de la Recherche Scientifique (CNRS), Paris (FR); Sorbonne Universite, Paris (FR)

( * ) Notice: Subject to any disclaimer, the term of this patent is extended or adjusted under 35 U.S.C. 154(b) by 1143 days.

(21) Appl. No.: 17/058,277

(22) PCT Filed: May 24, 2019

(86) PCT No.: PCT/EP2019/063521
§ 371 (c)(1),
(2) Date: Nov. 24, 2020

(87) PCT Pub. No.: WO2019/224375
PCT Pub. Date: Nov. 28, 2019

(65) Prior Publication Data
US 2021/0213410 A1 Jul. 15, 2021

(30) Foreign Application Priority Data

May 24, 2018 (FR) ..................................... 1854366

(51) Int. Cl.
*B01J 13/00* (2006.01)
*C09K 23/00* (2022.01)
*C12Q 1/02* (2006.01)
*G01N 15/10* (2024.01)

(52) U.S. Cl.
CPC ....... *B01J 13/0039* (2013.01); *B01J 13/0047* (2013.01); *C09K 23/00* (2022.01); *C12Q 1/02* (2013.01); *G01N 15/1012* (2013.01); *G01N 2015/1014* (2024.01)

(58) Field of Classification Search
CPC .................................................. A61K 49/0078
See application file for complete search history.

(56) References Cited

U.S. PATENT DOCUMENTS

| | | | |
|---|---|---|---|
| 5,118,528 A | 6/1992 | Fessi et al. | |
| 6,069,165 A | 5/2000 | Andrieu et al. | |
| 2009/0098171 A1 | 4/2009 | Alard et al. | |
| 2010/0144899 A1 | 6/2010 | Goutayer et al. | |
| 2010/0284932 A1 | 11/2010 | Goutayer et al. | |

FOREIGN PATENT DOCUMENTS

| | | |
|---|---|---|
| EP | 0275796 A1 | 7/1988 |
| EP | 0275796 B1 * | 3/1992 |
| FR | 2753376 A1 | 3/1998 |
| FR | 2828378 A1 | 2/2003 |
| FR | 2921253 A1 | 3/2009 |
| WO | 2008102065 A1 | 8/2008 |
| WO | 2014076432 A1 | 5/2014 |

OTHER PUBLICATIONS

EP 0275796 B1 Google translation (Year: 1992).*
Hadorn et al., PNAS, 2012; 109(50):20320-20325 (Year: 2012).*
Xiang et al., Chapter 7 The Applications of DMSO, published Oct. 27, 2017 (summary only) (Year: 2017).*
ACS Chemistry for life, https://www.acs.org/molecule-of-the-week/archive/d/dimethyl-sulfoxide.html#:~:text=DMSO%20is%20a%20laboratory%20and,used%20solvent%20for%20chemical%20reactions; Sep. 21, 2021 (Year: 2021).*
Jun. 19, 2019—(WO) International Search Report—Appln No. PCT/EP2019/063521.
M'Barek et al. "Phagocytosis of immunoglobulin-coated emulsion droplets" Biomaterials, vol. 51, Feb. 20, 2015, pp. 270-277.
Fattaccioli et al. "Size and fluorescence measurements of individual droplets by flow cytometry" Soft Matter, vol. 5, No. 11, Jan. 1, 2009, p. 2232.
Yang et al. "Role of phospholipids and copolymers in enhacing stability and controlling degradation of intravenous lipid emulsions" Colloids and Surfaces A: Physiochemical and Engineering Aspects, vol. 436, Jul. 22, 2013, pp. 434-442.
Salminen et al. "Formation of nanostructured colloidosomes using electrostatic deposition of solid lipid nanoparticles onto an oil droplet interface" Food Research International, vol. 79, Nov. 30, 2015, pp. 11-18.
Pontani et al. "Biomimetic emulsions reveal the effect of mechanical forces on cell-cell adhesion" Proc. Natl. Acad. Sci. U. S. A. 109 (2012) 9839.
Fattaccioli et al. "Specific wetting probeb with biomimetic emulsion droplets" Soft Matter 4 (2008) 2434.
Bourouina et al. "Formation of specific receptor-ligand bonds between liquid interfaces" Soft Matter 7 (2011) 9130.
Massart "Preparation of Aqueous Magnetic Liquids in Alkaline and Acidic Media" IEEE Trans. Magn. 17 (1981) 1247.
Hadorn et al. Specific and reversible DNA-directed self-assembly of oil-in-water emulsion droplets, Proc. Natl. Acad. Sci. U. S. A. 109 (2012) 20320-20325.
Feng et al. "Specificity, flexibility and valence of DNA bonds guide emulsion architecture" Soft Matter 9 (2013) 9816.
Thiam et al. "From Stability to Permeability of Adhesive Emulsion Bilayers", Langmuir 28 (2012) 6291.
Campàs et al. "Quantifying cell-generated mechanical forces within living embryonic tissues" Nat Methods. Feb. 2014 ; 11(2): 183-189.
Mason et al. "Emulsification in Viscoelastic Media" Phys. Rev. Lett. 77 (1996) 3481.
Mittal "Determination of CMC of Polysorbate 20 in Aqueous Solution by Surface Tension Method" J. Pharm. Sci. 61 (1972) 1334.

(Continued)

*Primary Examiner* — Brian Gangle
*Assistant Examiner* — Lakia J Jackson-Tongue
(74) *Attorney, Agent, or Firm* — Banner & Witcoff, Ltd.

(57) ABSTRACT

The present invention relates to a method for producing a colloid comprising functionalised liquid colloidal particles. The invention also relates to such a colloid and to the uses thereof.

15 Claims, 14 Drawing Sheets

(56) References Cited

OTHER PUBLICATIONS

Efremova et al. "Measurements of Interbilayer Forces and Protein Adsorption on Uncharged Lipid Bilayers Displaying Poly(ethylene glycol) Chains" Biochemistry 39 (2000) 3441.
Banks et al. "Anomalous Diffusion of Proteins Due to Molecular Crowding" Biophys. J. 89 (2005) 2960.
Werner et al. "The shape of Immunoglobulin G Molecules in Solution", Proc. Natl. Acad. Sci. U. S. A. 69 (1972) 795.
Xia et al. "Soft Lithography". Chemie Int. Ed. 37 (1998) 550.
Automatic Translation WO2014076432A1.
Automatic Translation FR2828378A1.

* cited by examiner

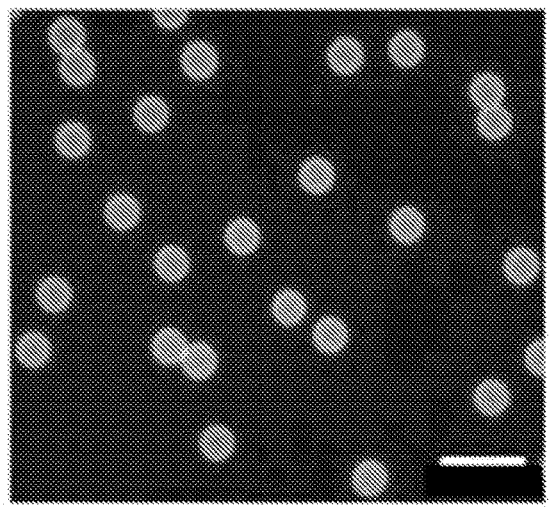
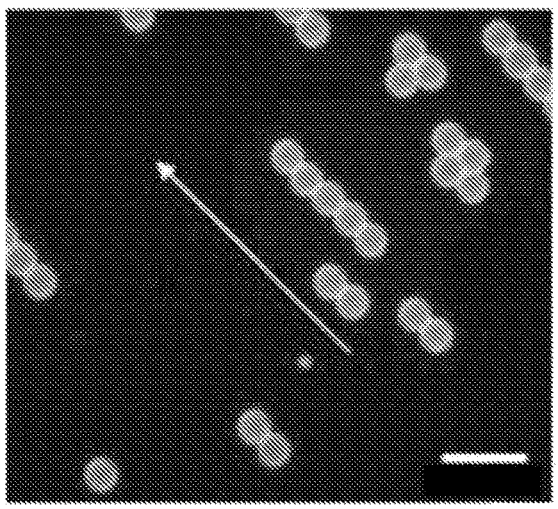
Fig. 13A
Fig. 13B
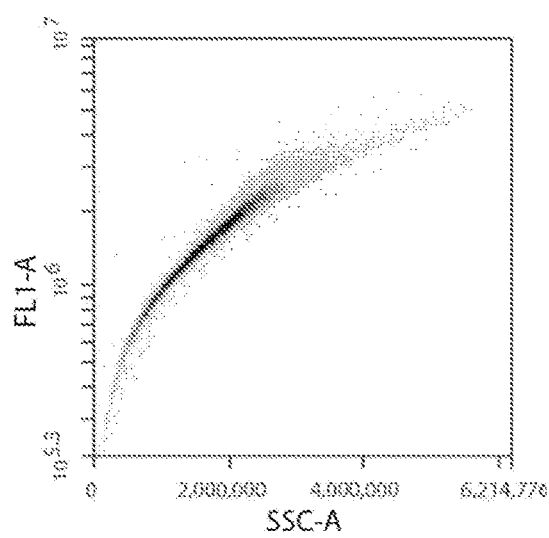
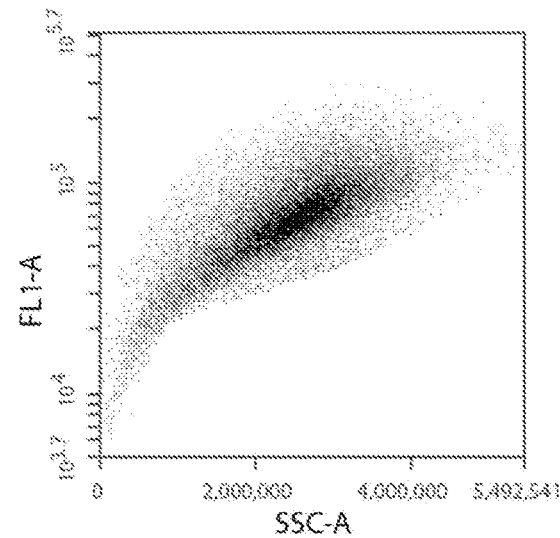
Fig. 14A
Fig. 14B

COLLOIDAL PARTICLES FUNCTIONALIZED HOMOGENEOUSLY BY BIOMOLECULES

RELATED APPLICATION DATA

This application is a National Stage Application under 35 U.S.C. 371 of co-pending PCT application number PCT/EP2019/063521 designating the United States and filed May 24, 2019; which claims the benefit of FR application number 1854366 and filed May 24, 2018 each of which are hereby incorporated by reference in their entireties.

The present invention relates to a method for producing a colloid comprising functionalized liquid colloidal particles.

Characterized by a fluid and deformable interface, liquid colloidal droplets (also called particles) are interesting from the following viewpoints: it is possible to vary their size and their volume and surface area composition, and notably to functionalize them with molecular units that may be fluorescent or recognized by cell membrane receptors.

Functionalized emulsion droplets have thus recently been used as biomimetic surfaces for modelling cellular adhesion [1-3] or as cellular probes to study phagocytosis[4].

In the literature, emulsion droplets functionalized by lipids are generally obtained by direct dissolution of lipids in an oil followed by the production of droplets [1, 5-6], using a carrier solvent insoluble in water, such as chloroform, for mixing the lipids with the oil before emulsification [4, 7] or by dissolving the lipids in water in the presence of the droplets after fragmentation [8].

Few studies have addressed measuring the homogeneity of lipid insertion on the surface of the droplets at the scale of the entire suspension, but those that have done so showed a significant variation from one droplet to another within the same emulsion when the lipids are dissolved in the hydrophobic phase before emulsification. For lipids dissolved directly in water, their low solubility and their tendency to form metastable aggregates such as liposomes is also a limitation in terms of the efficacy of functionalization.

In order to alleviate these problems, the inventors developed a new droplet functionalization protocol enabling to improve the homogeneity and insertion kinetics of lipids on the surface of the droplets within a given emulsion.

Instead of dissolving lipids in oil, with or without a carrier solvent, before emulsification, the method according to the present invention involves prior fabrication of droplets, followed by insertion of lipids on the surface of the droplets in a second step (FIG. 1). It relies on the use of a polar co-solvent promoting lipid dissolution in the aqueous continuous phase, and enables droplets to be obtained that are distinguished by very substantial homogeneity and rapidity of functionalization.

Such droplets can especially be used for flow cytometer calibration.

In a flow cytometer, individual objects such as cells, beads or bacteria are illuminated by a laser beam and several parameters are recorded for each of them: forward scatter channel (FSC) and side scatter channel (SSC), which give information on the size and shape of objects, and the fluorescence intensities. The fluorescence-related parameters are used to quantify, classify and sort objects in the presence of intrinsic or extrinsic fluorescent compounds.

A flow cytometer requires rigorous optical alignment and precise calibration of the light sources and detectors to provide reliable measurements. Calibration is commonly done by using micrometer-sized fluorescent beads. These beads are characterized by a pronounced monodispersity in size, obtained thanks to their synthesis method, and a very small variation in fluorescence within the same sample. These solid particles nevertheless tend to aggregate over time during storage, which makes measurements more difficult to perform.

More recently, it has been proposed to use emulsions calibrated in size and made fluorescent by dissolving a fluorophore in the volume of the hydrophobic phase or by functionalizing the surface of the droplets with fluorescent molecules or biomolecules. The fact that traditional protocols do not allow obtaining good fluorescence homogeneity is a technological barrier that the present invention makes it possible to overcome.

The present invention relates firstly to a method for obtaining a colloid comprising functionalized liquid colloidal particles comprising the following steps:
   a) dispersing an oil 1 in an aqueous solution 2 comprising a fragmentation surfactant leading to obtaining an emulsion 3 comprising oil droplets suspended in an aqueous phase;
   b) dissolving lipids aimed at functionalizing said oil droplets in a polar aprotic solvent, leading to obtaining a functionalization solution 4;
   c) preparing a functionalization mixture 5, comprising emulsion 3 and functionalization solution 4, the volume fraction of the polar aprotic solvent in said functionalization mixture 5 being comprised between 1 and 15%, preferably between 5 and 15%, advantageously between 8 and 15%;
   d) incubating functionalization mixture 5, during which at least a part of the lipids initially present in functionalization solution 4 are adsorbed on the surface of the oil droplets initially present in emulsion 3; and
   e) eliminating non-adsorbed lipids during step d);
thus allowing to obtain a colloid comprising functionalized liquid colloidal particles consisting of the oil droplets obtained after step a) on the surface of which the lipids are adsorbed during step d).

Any oil known to the person skilled in the art to form oil-in-water emulsions may be used in step a). In particular, oil 1 dispersed in aqueous solution 2 can be a mineral oil, a vegetable oil such as soybean oil, a silicone oil, a halogenated oil (in particular a fluorinated oil, an iodinated oil or a brominated oil), an animal oil such as squalene or a mixture of these.

The liquid core of the oil droplets may comprise one or more active agents, chosen from among cosmetic, pharmaceutical or comestible agents or lubricants, which can be hydrophilic or hydrophobic. The liquid core can optionally comprise solid particles in suspension, such as metal nanoparticles, mineral particles or composite particles, for instance. Advantageously, when they are present, the size of said particles is comprised from 10 nm to 10 μm. The liquid core may optionally comprise liquid particles in suspension, such as water-in-oil type emulsion droplets; the size of said particles is comprised from 10 nm to 10 μm.

In one particular embodiment, oil 1 is a vegetable oil, notably soybean oil.

In one particular embodiment, oil 1 is a mineral oil optionally comprising nanoparticles of $Fe_2O_3$ in suspension.

In the present invention, "fragmentation surfactant" means any molecule known to the skilled person facilitating dispersion of oil 1 in aqueous solution 2. It may be a natural or synthetic anionic, cationic, zwitterionic or nonionic surfactant.

Anionic surfactants include notably salts (e.g. sodium salts) of linear or branched, saturated or unsaturated fatty alcohol sulfate having 8 to 20 carbon atoms, such as sodium lauryl sulfate (also called sodium dodecyl sulfate or SDS).

Cationic surfactants include notably cetrimonium bromide or chloride (also called hexadecyltrimethylammonium bromide and chloride or CTAB and CTAC).

Zwitterionic surfactants include notably betaines such as coco-betaine (also called cocamidopropyl betaine or CAPB).

Nonionic surfactants include notably polyoxyethylene sorbitan esters (known under the brand name "Tween"), polyethylene glycol ethers (in particular the commercial "Brij" and "Triton" lines) and poloxamers (known under the brand name "Pluronic"), such as Pluronic F-68.

In one particular embodiment, the fragmentation surfactant is a poloxamer such as Pluronic F-68.

Step a) is an emulsification step, which may be implemented according to any of the methods well known to the skilled person. Oil 1 can notably be dispersed in aqueous solution 2 by manual emulsification, by means of membranes, a Couette emulsifier or a microfluidic device, or according to the method described by Obey and Vincent [J. Colloid Interface Sci. 163, 454 (1994)].

At the end of step a), the oil droplets obtained in suspension in the aqueous phase of emulsion 3 have a diameter comprised between 1 and 20 µm, in particular comprised between 2 and 15 µm, advantageously between 3 and 10 µm.

The droplet diameter is determined by microscopy and image analysis, as described in the examples.

In the present invention, "polar aprotic solvent" means a solvent that has a non-zero dipole moment and that does not comprise any acid hydrogen, i.e., no hydrogen atom bound to a heteroatom such as N, O or S. It may notably be a ketone, a sulfoxide, an N,N-disubstituted amide, an ester, a tertiary amine or a heterocycle.

In the present invention, "ketone" means an $R_1$—CO—$R_2$ compound, wherein $R_1$ and $R_2$ are identical or different ($C_1$-$C_6$)alkyl groups. Examples include propanone and butanone.

In the present invention, "sulfoxide" means an $R_3$—SO—$R_4$ compound, wherein $R_3$ and $R_4$ are identical or different ($C_1$-$C_6$)alkyl groups. Examples include dimethylsulfoxide (DMSO).

In the present invention, "N,N-disubstituted amide" means an $R_5$—CO—$NR_6R_7$ compound, wherein $R_5$ is a hydrogen atom or a ($C_1$-$C_6$)alkyl group, and $R_6$ and $R_7$ are identical or different ($C_1$-$C_6$)alkyl groups. Examples include N,N-dimethylformamide (DMF).

In the present invention, "ester" means an $R_9$—COO—$R_{10}$ compound, wherein $R_9$ and fro are identical or different ($C_1$-$C_6$)alkyl groups. The ester may particularly be an acetate, i.e., a $CH_3COO$—$R_{10}$ compound. Examples include ethyl acetate.

In the present invention, "tertiary amine" means an $NR_{11}R_{12}R_{13}$ compound, wherein $R_{11}$, $R_{12}$ and $R_{13}$ are identical or different ($C_1$-$C_6$)alkyl groups. Examples include triethylamine.

In the present invention, "($C_1$-$C_6$)alkyl" group means a linear or branched hydrocarbon chain comprising 1 to 6 carbon atoms, preferably 1 to 4 carbon atoms. Examples include methyl, ethyl, propyl, isopropyl, butyl, isobutyl, sec-butyl, tert-butyl, pentyl or hexyl groups.

In the present invention, "heterocycle" means a saturated or unsaturated, aromatic or nonaromatic ring containing one or more heteroatoms, such as, for example, sulfur, nitrogen or oxygen atoms. In particular, it can be a 5- or 6-member heterocycle advantageously containing 1 to 4, more advantageously 1 or 2, heteroatoms. Examples include pyridine.

In particular, the polar aprotic solvent is selected from the group consisting of DMSO, ethyl acetate, acetonitrile, pyridine, butanone, triethylamine, N,N-dimethylformamide (DMF), and mixtures thereof. Preferably it is a sulfoxide such as DMSO.

Any natural or synthetic amphiphilic lipid known to the skilled person, may be used during step b) resulting in obtaining functionalization solution 4.

It may or may not be a fluorescent lipid. Fluorescent lipids include 1,2-dioleoyl-sn-glycero-3-phosphoethanolamine carboxyfluorescein (also called DOPE CF).

In one embodiment, the lipids are phospholipids, in particular phosphoglycerides, phosphorylated sphingolipids or phosphatidylinositols.

Phosphoglycerides include notably phosphatidylethanolamines, such as 1,2-dioleoyl-sn-glycero-3-phosphoethanolamine (DOPE) and 1,2-distearoyl-sn-glycero-3-phosphoethanolamine (DSPE); phosphatidylcholines and phosphatidylserines.

Phosphorylated sphingolipids include notably sphingosine-1-phosphate.

Phosphatidylinositols include notably glycophosphatidylinositols (GPI).

Advantageously, the lipids are phospholipids, in particular phosphatidylethanolamines such as DOPE or DSPE.

In one particular embodiment, the lipids comprise at least one fluorophore group and/or at least one biomolecule, that can be grafted via a linker.

Said linker may be initially present in the lipid used in step b) or grafted later.

It can comprise, for example, a polyethylene glycol (PEG) chain, or a nitriloacetate (NTA) group optionally complexed to nickel (Ni-NTA). Advantageously, it is a PEG chain.

Examples of the fluorophore group include 6-carboxyfluorescein (CF), fluorescein, rhodamine, commercial fluorophores of the "Alexa Fluor" and "DyLight" lines, advantageously 6-carboxyfluorescein.

The biomolecule may notably be a vitamin, such as biotin, a peptide, such as arginyl-glycyl-aspartic acid (RGD), a protein, such as streptavidin, an enzyme, an antibody, notably a type G immunoglobulin (IgG) or a combination thereof.

It may or may not be fluorescent, and its fluorescence may be intrinsic or result from the presence of a fluorophore group.

It may be initially comprised in the lipid used in step b) or grafted later as described below.

Advantageously, the biomolecule is a biotin. In the description that follows, a lipid grafted with biotin by means of a PEG chain can be designated by the term "biotinylated lipid."

In another particular embodiment, the lipids are phospholipids, in particular phosphatidylethanolamines such as DOPE or DSPE, optionally grafted with at least one fluorophore group and/or at least one biomolecule, optionally via a linker.

In particular, the lipids are selected from the group consisting of DOPE-CF, DSPE-PEG-RGD, DSPE-PEG-biotin and mixtures thereof. Advantageously, the lipids are selected from the group consisting of DOPE-CF, DSPE-PEG-biotin and mixtures thereof.

In one embodiment, a dispersion surfactant is added at step c).

In the present invention, "dispersion surfactant" means any amphiphilic molecule that prevents the formation of aggregates.

Preferably, the dispersion surfactant optionally added at step c) does not denature proteins.

In particular, it is a nonionic surfactant, particularly a polyoxyethylene sorbitan ester or a polyethylene glycol ether ("Tween" or "Brij" lines), or a poloxamer, or a zwitterionic surfactant, such as a sulfobetaine.

Advantageously, the dispersion surfactant added in step c) is Tween 20 or Pluronic F-68.

When a dispersion surfactant is added in step c), its concentration in functionalization mixture 5 is less than 5 times its critical micelle concentration (CMC), preferably less than 2 times its CMC, notably less than 1.5 times its CMC, advantageously less than or equal to its CMC.

In one embodiment, a buffer solution 6 is added at step c). Preferably, its pH is comprised between 5 and 9, especially between 6 and 8, for example its pH equals around 7. It may notably be a phosphate buffer.

The volume fraction of the polar aprotic solvent in functionalization mixture 5 obtained in step c) is comprised between 1 and 15%, preferably between 5 and 15%, advantageously between 8 and 15%.

In one embodiment, incubation step d) is performed at a temperature comprised between 15° C. and 40° C., preferably between 20° C. and 30° C., and advantageously for a duration comprised between 10 min and 10 h, preferably between 30 min and 5 h, advantageously between 1 h and 3 h.

In one particular embodiment, oil 1 dispersed in aqueous solution 2 comprises $Fe_2O_3$ in suspension. The implementation of such a method according to the invention thus allows to obtain a colloid comprising magnetic functionalized liquid colloidal particles.

In this embodiment, oil 1 is preferably a mineral oil.

In one particular embodiment, oil 1 dispersed in aqueous solution 2 has a density greater than 1. The implementation of such a method according to the invention thus allows to obtain a colloid comprising functionalized liquid colloidal particles that are denser than the aqueous phase of the colloid.

In this embodiment, oil 1 is preferably a halogenated oil.

In one embodiment, the method according to the invention comprises, after step e), an additional step f) of grafting biomolecules onto the lipids adsorbed on the surface of the oil droplets.

The biomolecules grafted during this step f) may notably be vitamins, peptides, proteins, such as streptavidin, enzymes, antibodies, especially type G immunoglobulins (IgGs).

They may or may not be fluorescent, and their fluorescence may be intrinsic or result from the presence of a fluorophore group.

In particular, when the lipids adsorbed on the surface of the oil droplets are biotinylated lipids, streptavidin, avidin, monomeric avidin, neutravidin molecules or anti-biotin IgG may be grafted in step f).

A second object of the present invention concerns a colloid comprising functionalized liquid colloidal particles that can be obtained by the method described previously.

Moreover, the present invention also relates to a colloid comprising functionalized liquid colloidal particles in suspension in a liquid,
  said liquid consisting of an aqueous solution comprising a polar aprotic solvent, the volume fraction of said polar aprotic solvent in said liquid being comprised between 1 and 15%, preferably between 5 and 15%, advantageously between 8 and 15%; and
  said functionalized liquid colloidal particles consisting of oil droplets on the surface of which lipids are adsorbed.

In particular, the polar aprotic solvent is as defined previously and advantageously selected from the group consisting of DMSO, ethyl acetate, acetonitrile, pyridine, butanone, triethylamine, N,N-dimethylformamide (DMF), and mixtures thereof. Preferably it is a sulfoxide such as DMSO.

The oil can be a mineral oil, a vegetable oil such as soybean oil, a silicone oil, a halogenated oil (in particular a fluorinated oil, an iodinated oil or a brominated oil), or a mixture thereof.

In one particular embodiment, the oil droplets are mineral oil droplets and comprise nanoparticles of $Fe_2O_3$ in suspension.

In another embodiment, the oil has a density greater than 1. Preferably it is a halogenated oil.

Any natural or synthetic amphiphilic liquid known to the skilled person can be adsorbed at the surface of the oil droplets.

It may or may not be a fluorescent lipid. Fluorescent lipids include notably 1,2-dioleoyl-sn-glycero-3-phosphoethanolamine carboxyfluorescein (also called DOPE CF).

In one embodiment, the lipids are phospholipids, in particular phosphoglycerides, phosphorylated sphingolipids or phosphatidylinositols.

Phosphoglycerides include notably phosphatidylethanolamines, such as 1,2-dioleoyl-sn-glycero-3-phosphoethanolamine (DOPE) and 1,2-distearoyl-sn-glycero-3-phosphoethanolamine (DSPE); phosphatidylcholines and phosphatidylserines.

Phosphorylated sphingolipids include notably sphingosine-1-phosphate.

Phosphatidylinositols include notably glycophosphatidylinositols (GPI).

Advantageously, the lipids are phospholipids, in particular phosphatidylethanolamines such as DOPE or DSPE.

In one particular embodiment, the lipids comprise at least one fluorophore group and/or at least one biomolecule, that can be grafted via a linker.

Said linker can comprise a polyethylene glycol (PEG) chain, or a nitriloacetate (NTA) group optionally complexed to nickel (Ni-NTA). Advantageously, it is a PEG chain.

Examples of the fluorophore group include 6-carboxyfluorescein (CF), fluorescein, rhodamine, commercial fluorophores of the "Alexa Fluor" and "DyLight" lines, advantageously 6-carboxyfluorescein.

The biomolecule may notably be a vitamin, such as biotin, a peptide, such as arginyl-glycyl-aspartic acid (RGD), a protein, such as streptavidin, an enzyme, an antibody, particularly a type G immunoglobulin (IgG) or a combination thereof.

It may or may not be fluorescent, and its fluorescence may be intrinsic or result from the presence of a fluorophore group.

Advantageously, the biomolecule is a biotin, typically grafted via a PEG chain.

The PEG-biotin fragment can then itself represent a linker, onto which a biomolecule can be grafted having an affinity for biotin, such as streptavidin, avidin, monomeric avidin, neutravidin or an anti-biotin IgG.

In another embodiment, the lipids are phospholipids, in particular phosphatidylethanolamines such as DOPE or DSPE, optionally grafted with at least one fluorophore group and/or at least one biomolecule, optionally via a linker.

In particular, the lipids are selected from the group consisting of DOPE-CF, DSPE-PEG-RGD, DSPE-PEG-biotin and mixtures thereof. Advantageously, the lipids are selected from the group consisting of DOPE-CF, DSPE-PEG-biotin and mixtures thereof.

In one particular embodiment, the colloid is such that, within a subpopulation of particles having a diameter equal to d+/−15%, the coefficient of variation of the quantity of lipid adsorbed at the droplet surface is less than or equal to 20%.

The present invention additionally relates to the use of a colloid as described previously for calibrating a flow cytometer.

The present invention additionally relates to the use of a colloid comprising functionalized liquid colloidal particles that can be obtained by the method of the present invention for the calibration of a flow cytometer.

The present invention also relates to the use of a colloid as described previously for the study of their ingestion by cells, such as phagocytosis by macrophages. Advantageously, the density of the oil making up the functionalized liquid colloidal particles is greater than 1. Typically, it is a halogenated oil.

The present invention additionally relates to the use of a colloid comprising functionalized liquid colloidal particles that can be obtained by the method of the present invention for the study of their ingestion by cells, such as phagocytosis by macrophages. Advantageously, the density of the oil making up the functionalized liquid colloidal particles is greater than 1. Typically, it is a halogenated oil.

FIGURES

Figure 3A:
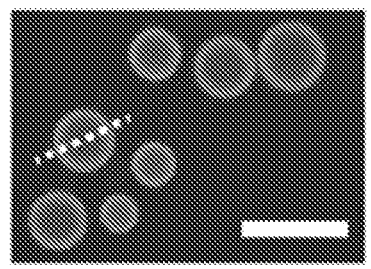
FIG. 3A is the image of droplets functionalized by DOPE-CF recorded by spinning disk confocal microscopy (scale bar=15 μm).
Figure 3B:
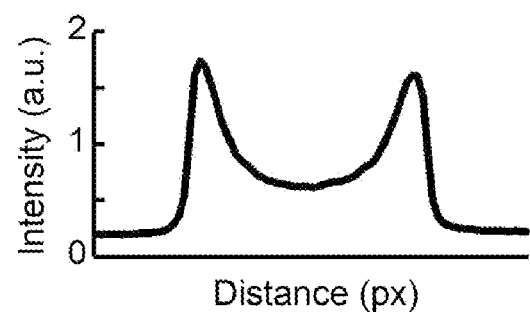
FIG. 3B shows the fluorescence profile of a droplet of FIG. 3A (see dotted line, FIG. 3A).
Figure 3C:
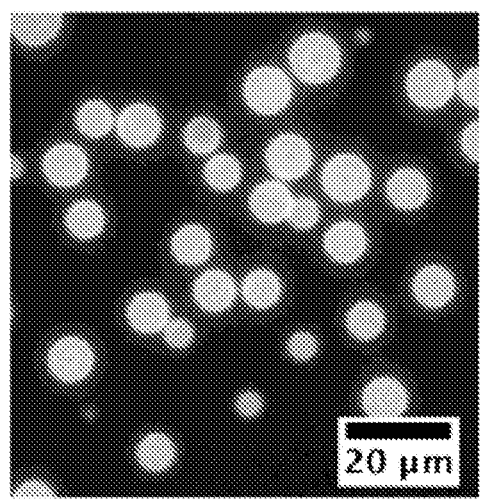
FIG. 3C is the image of emulsion A functionalized by DOPE-CF taken by wide-field epifluorescence microscopy with a 40× objective. The droplets show a homogeneous fluorescence due to the depth of field of the objective (scale bar=20 μm).
Figure 3D:
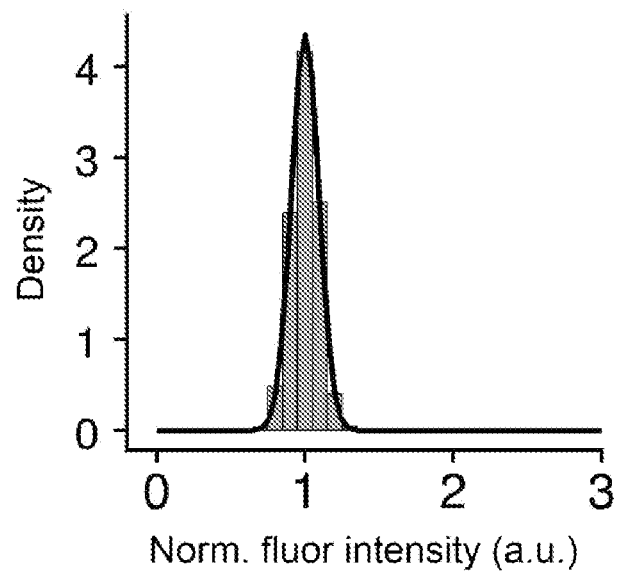

FIG. 3D shows the fluorescence distribution of a sub-sample of an emulsion of diameter equal to 8±1 μm (emulsion C) functionalized by DOPE-CF. The experimental data are measured by wide-field epifluorescence along a normal distribution (CV=8%). The fluorescence intensities are normalized relative to the mean of the sub-assembly.

Figure 3E:
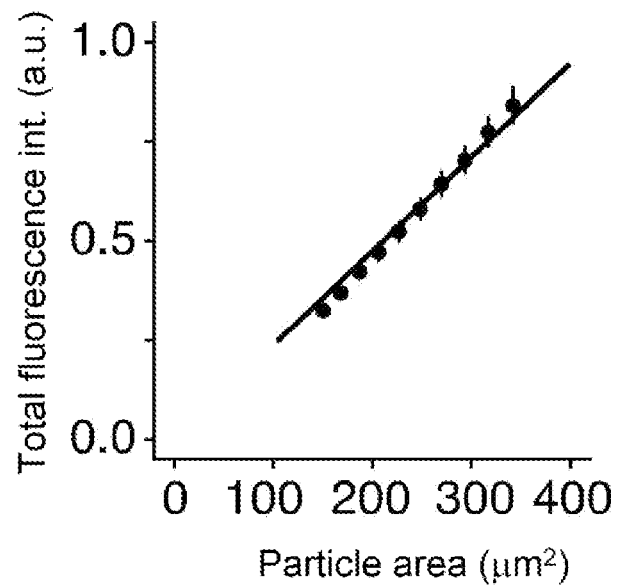

FIG. 3E shows the integrated fluorescence intensity of emulsion droplets functionalized by DOPE-CF (5 eq.) as a function of the square of the droplet radius ($R^2$) and measured by epifluorescence microscopy. The experimental data follow a linear function.

Figure 4:
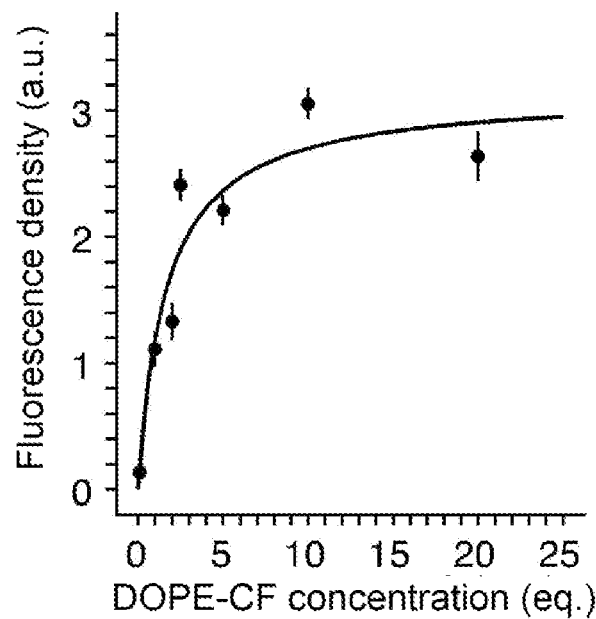

FIG. 4 is the titration curve for droplets functionalized by DOPE-CF. The droplet fluorescence density, i.e., the total fluorescence per object divided by its surface area in the images, is represented as a function of the DOPE-CF concentration, expressed in surface equivalent relative to a single layer.

Figure 5:
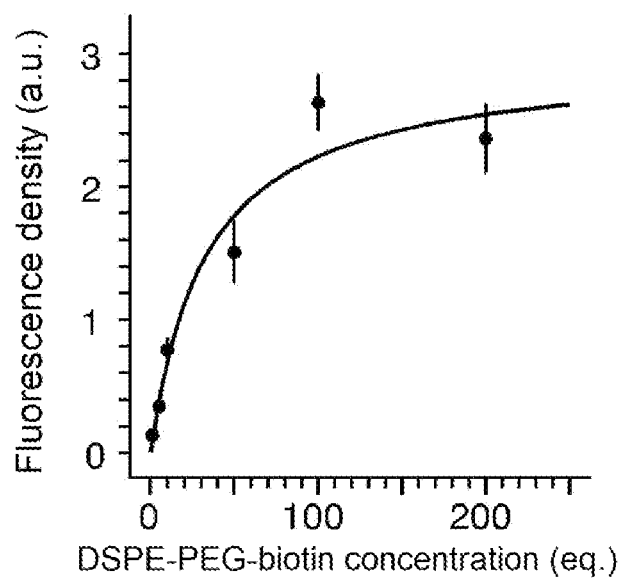

FIG. 5 is the titration curve of droplets functionalized by DSPE-PEG-biotin relative to the biotinylated lipid concentration. After insertion of the non-fluorescent biotinylated lipid, fluorescent IgGs are added to the aqueous phase at a saturation concentration of 5 eq.

Figure 6A:
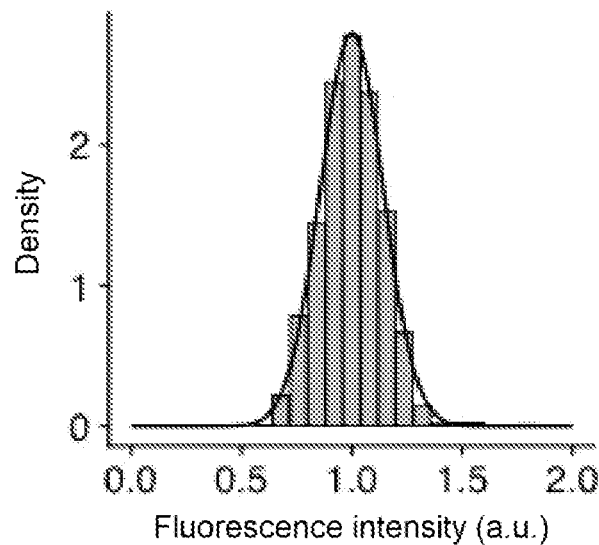
Figure 6B:
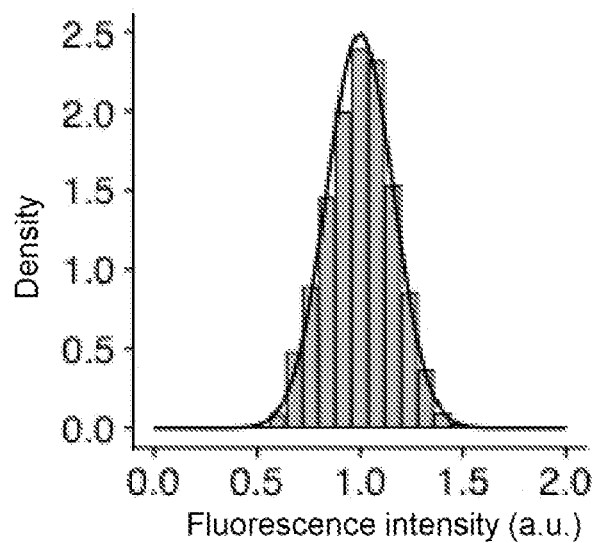

FIGS. 6A and 6B show the fluorescence distributions obtained for the droplets of emulsion C functionalized by DSPE-PEG-biotin-streptavidin (FIG. 6A) or DSPE-PEG-biotin-IgG (FIG. 6B). The coefficients of variation are 14% and 16%, respectively.

Figure 7A:
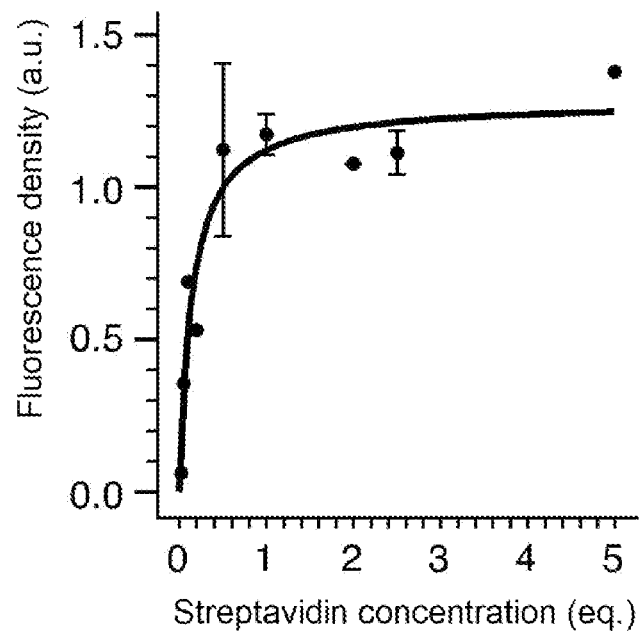
Figure 7B:
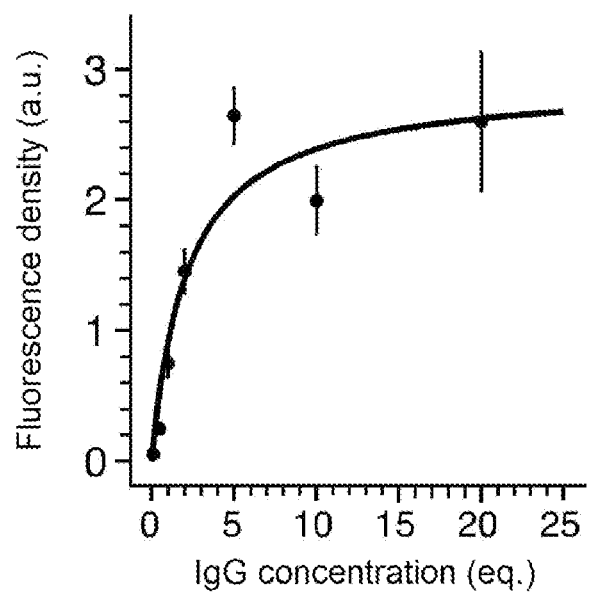

FIGS. 7A and 7B are the titration curves obtained for grafting streptavidin (FIG. 7A) and anti-biotin IgG (FIG. 7B) to droplets functionalized by DSPE-PEG-biotin.

Figure 8A:
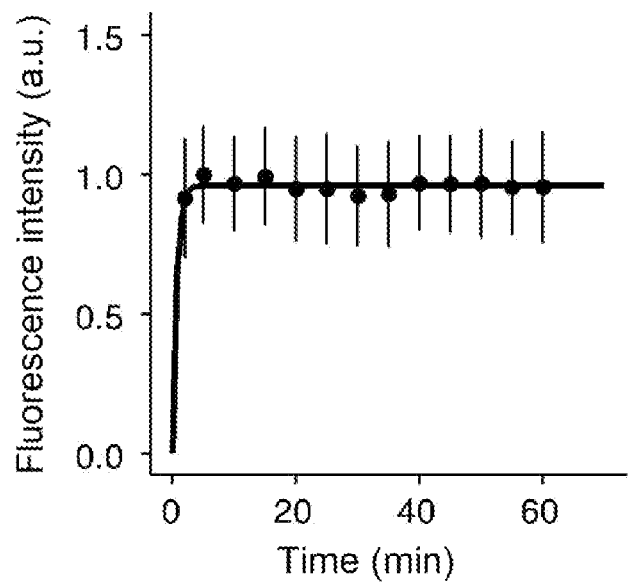
Figure 8B:
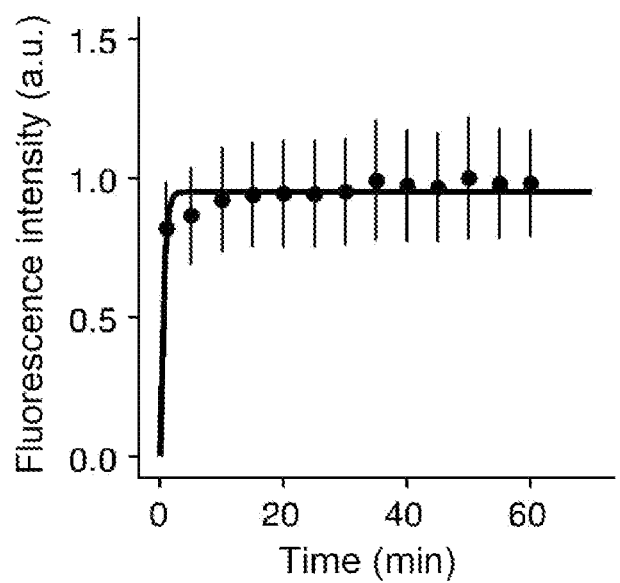

FIGS. 8A and 8B show the grafting kinetics for streptavidin (FIG. 8A) and anti-biotin IgG (FIG. 8B) to biotinylated droplets, determined by fluorescence measurements performed with a flow cytometer. The droplets were biotinylated with a solution of DSPE-PEG-biotin (100 eq.) containing 10% v/v of DMSO. The error bars correspond to the standard deviation calculated from N=3 independent experiments. The experimental data are the first order kinetics in both cases.

Figure 9A:
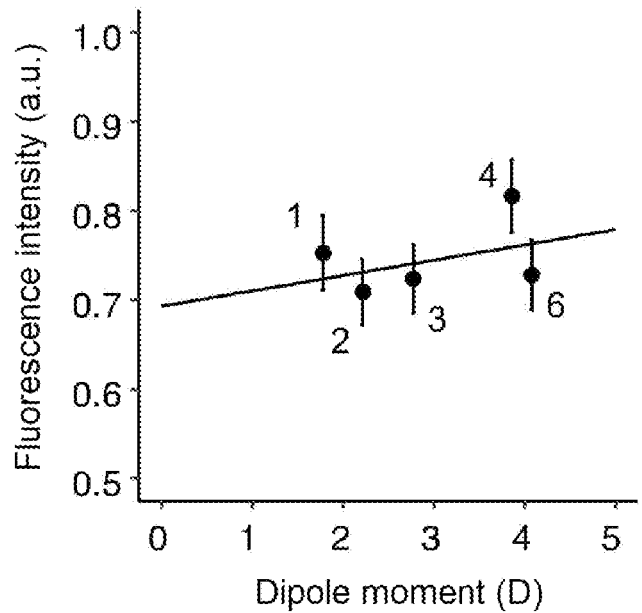
Figure 9B:
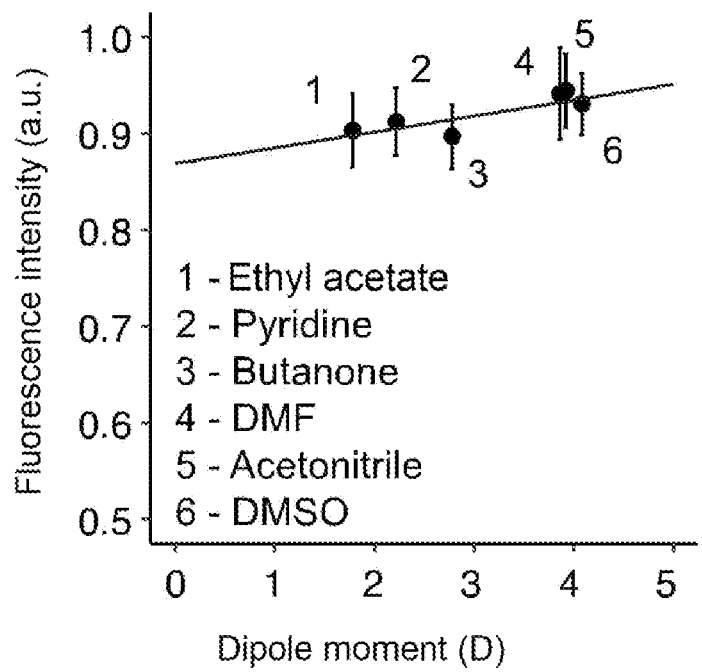

FIGS. 9A and 9B show the total fluorescence intensity measured by flow cytometry for droplets functionalized by DOPE-CF (FIG. 9A) or DSPE-PEG-biotin (FIG. 9B) onto which fluorescent IgGs are then grafted, as a function of the dipole moment of the solvent used in the functionalization solution.

Figure 10A:
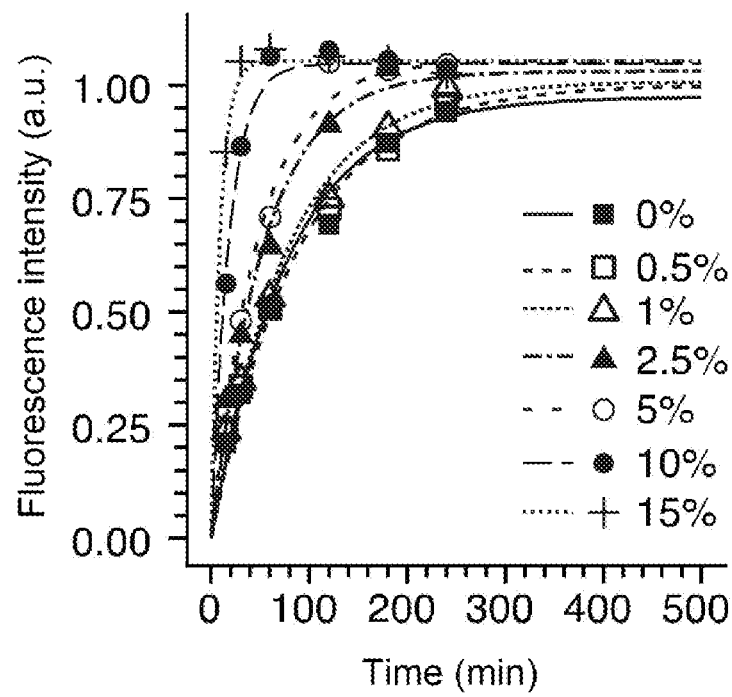

FIG. 10A shows the total fluorescence intensity measured for droplets functionalized by DOPE-CF, as a function of time, for volume fractions in DMSO in the continuous phase during the lipid adsorption step varying from 0 to 15% v/v. For each point indicated on the graph, the droplets were functionalized by using a DOPE-CF concentration of 2.5 equivalents.

Figure 10B:
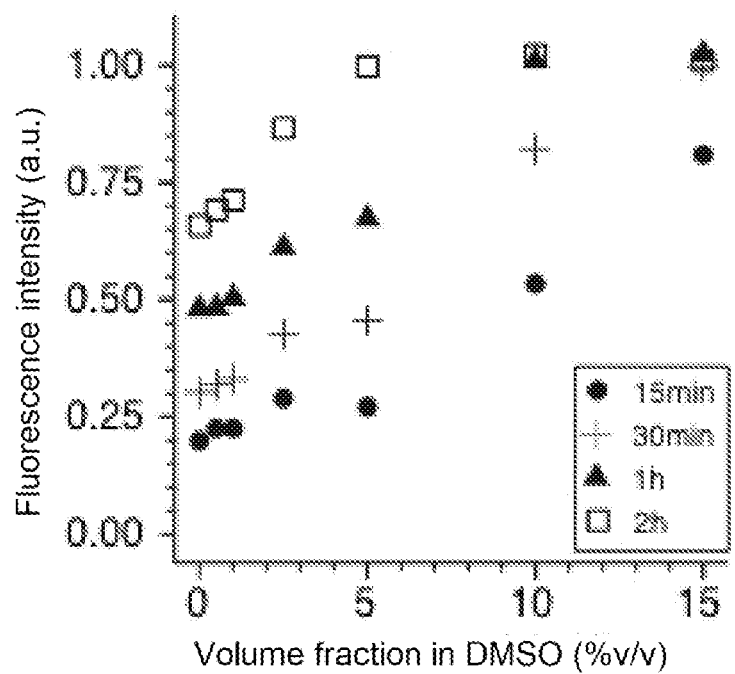

FIG. 10B shows the total fluorescence intensity measured for droplets functionalized by DOPE-CF of 2.5 equivalents, as a function of the volume fraction in DMSO in the continuous phase during the lipid adsorption step varying from 0 to 15% v/v, for reaction times of 15, 30, 60 and 120 min. The droplet fluorescence was measured by flow cytometry.

Figure 11:
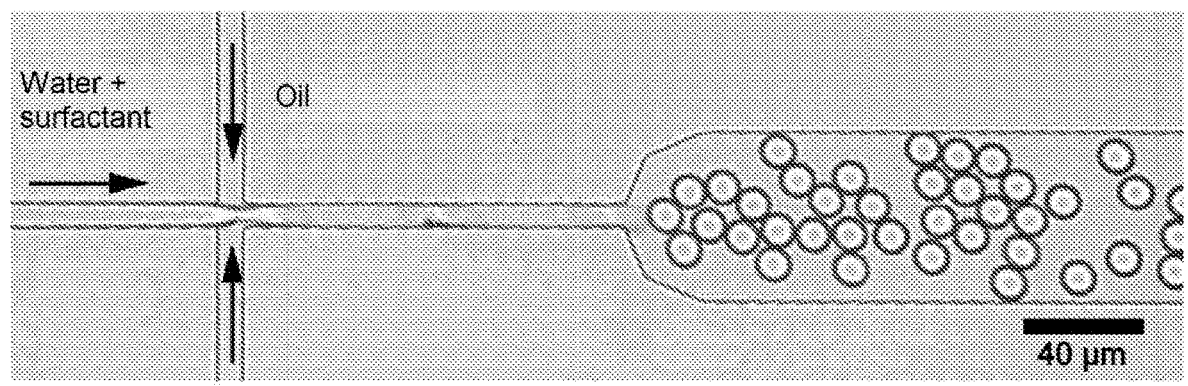

FIG. 11 shows a bright-field image of the microfluidic flow focusing device used for the production of monodispersed magnetic droplets.

Figure 12A:
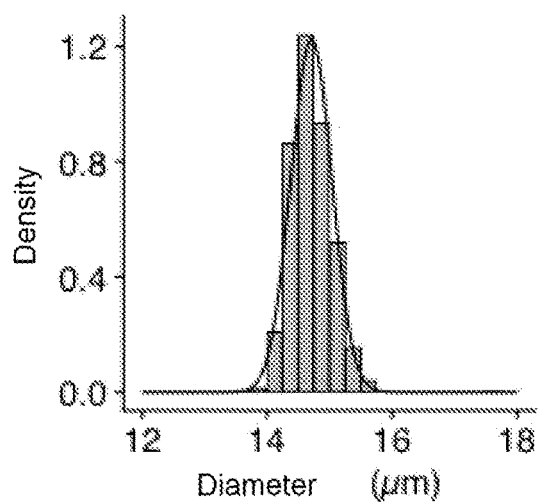
Figure 12B:
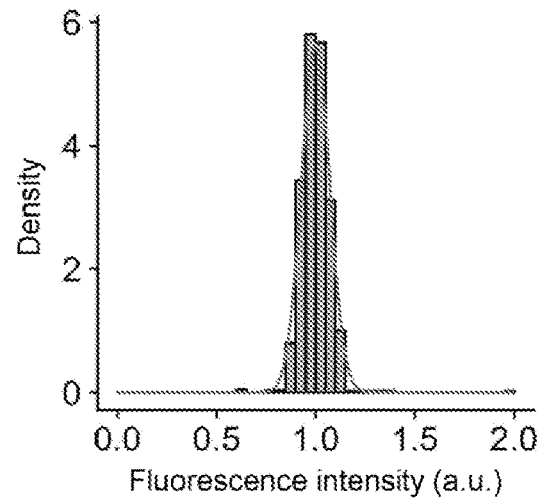

FIGS. 12A and 12B represent distributions of size (FIG. 12A) and fluorescence (FIG. 12B) of biotinylated magnetic droplets grafted with fluorescent anti-biotin IgGs obtained by the preceding device. The droplets have a diameter equal to 14.7 μm±2% and a fluorescence CV equal to 10%.

FIGS. 13A and 13B show the distribution of magnetic biotinylated droplets conjugated to fluorescent anti-biotin IgGs without (FIG. 13A) or with (FIG. 13B) application of a magnetic field (scale bar: 30 μm).

FIG. 14A is a diagram of density FL vs. SS obtained by flow cytometry in the case of droplets functionalized by DSPE-PEG-biotin according to the method of the invention then grafted with fluorescent anti-biotin IgGs.

FIG. 14B is a diagram of density FL vs. SS obtained by flow cytometry in the case of droplets functionalized by DSPE-PEG-biotin according to a protocol of the prior art (in which the lipids are diluted in oil before emulsification) then grafted with fluorescent anti-biotin IgGs.

Figure 15A:
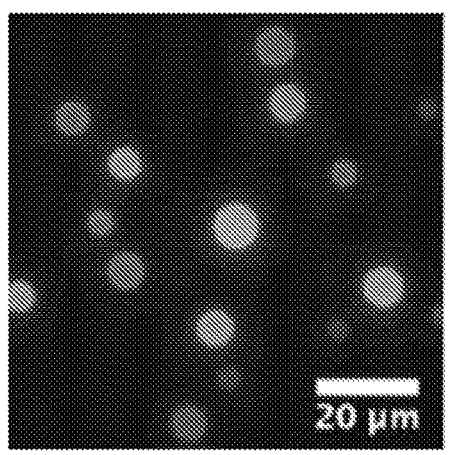

FIG. 15A is an image taken by wide-field epifluorescence microscopy of droplets (mean diameter 8 μm) functionalized by DSPE-PEG-biotin according to the protocol of the prior art (in which the lipids are diluted in oil before emulsification) then grafted with fluorescent anti-biotin IgGs (scale bar: 20 μm).

Figure 15B:
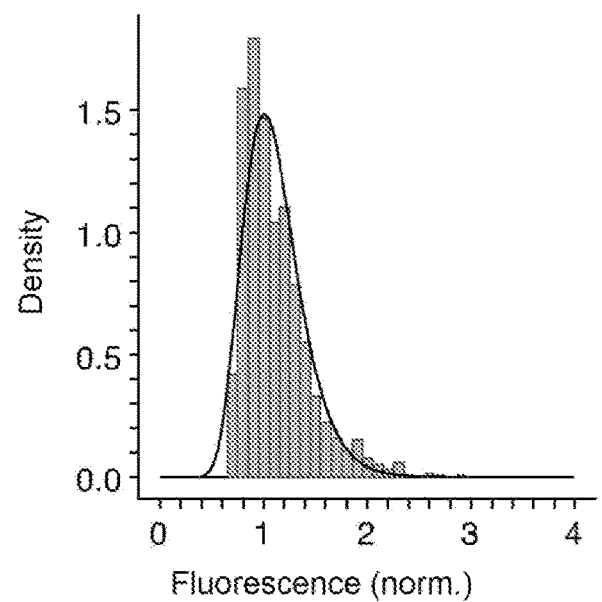

FIG. 15B shows the normalized fluorescence distribution of the preceding droplets (FIG. 15A). The experimental data correspond to a log-normal distribution ($\mu$=−0.31; $\sigma$=0.78; CV=92%). The fluorescence intensities are normalized relative to the mean value of the entire population.

Figure 16A:
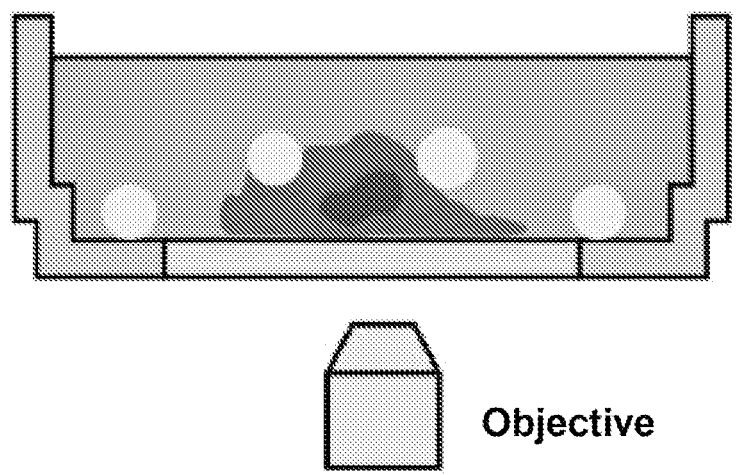

FIG. 16A is a schematic representation of the device used during phagocytosis experiments. The cells are placed at the bottom of a Petri dish provided with an optical glass bottom. The functionalized droplets are dispersed in the culture medium, sediment by gravity, come into contact with the cells and are eventually internalized.

Figure 16B:
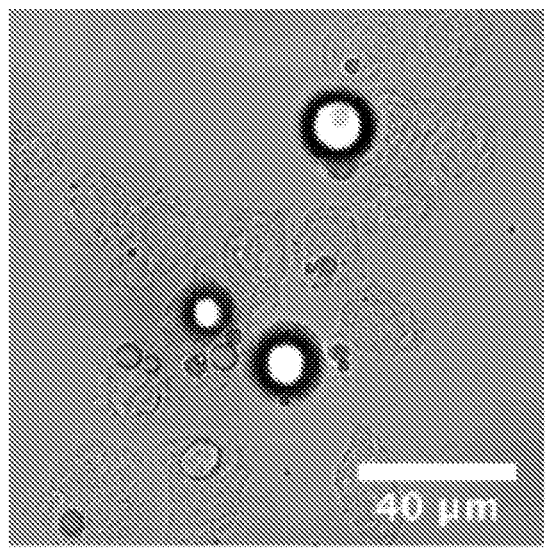
Figure 16C:
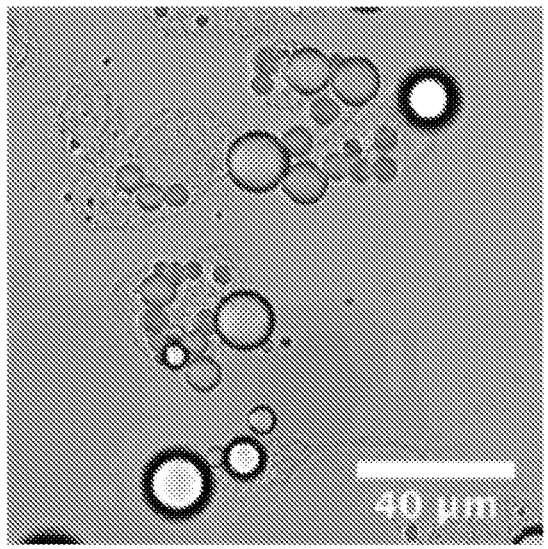

FIG. 16B is a bright-field microscopy image showing a phagocytosis experiment for oil droplets denser than the culture medium functionalized by IgGs when they are contacted with macrophages of the lineage. FIG. 16C shows the control experiment, performed with droplets not having IgG on the surface.

EXAMPLES

The following abbreviations were used:
BSA: bovine serum albumin
CF: 6-carboxyfluorescein
CMC: critical micelle concentration
CV: coefficient of variation
DMEM: Dulbecco Modified Eagle Medium
DMF: N,N-dimethylformamide
DMSO: dimethylsulfoxide
DOPE-CF: 1,2-dioleoyl-sn-glycero-3-phosphoethanolamine-N-(carboxyfluoresceine)
DSPE-PEG-biotin: 1,2-distearoyl-sn-glycero-3-phosphoethanolamine-N-[biotinyl (polyethylene glycol)-2000]
IgG: immunoglobulin G
PB: phosphate buffer
PBS: phosphate buffer saline
PDMS: polydimethylsiloxane
Materials and Methods A) Materials Soybean oil (CAS No. 8001-22-7), mineral oil (CAS No. 8042-47-5), Pluronic F-68 (CAS No. 9003-11-6), Tween 20 (CAS No. 9005-64-5), oleic acid (CAS No. 112-80-1), sodium alginate (CAS No. 9005-38-3), DMSO, acetonitrile, DMF, pyridine, butanone, ethyl acetate and triethylamine were purchased from Sigma-Aldrich (St Quentin Fallavier, France).

DOPE-CF and DSPE-PEG-biotin were purchased from Avanti Polar Lipids.

Mouse anti-biotin IgG conjugated to Alexa Fluor 488 (Ref. 200-542-211) was purchased from Jackson Immunoresearch (West Grove, Pa., USA).

FluoProbes 488 streptavidin was purchased from Interchim.

B) Fabrication of the Emulsion with a Couette Emulsifier

Figure 1:
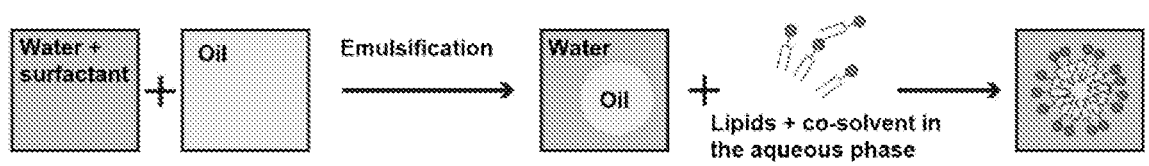
FIG. 1 is a schematic representation of the protocol for obtaining emulsion droplets functionalized by lipids according to the invention.
Figure 2A:
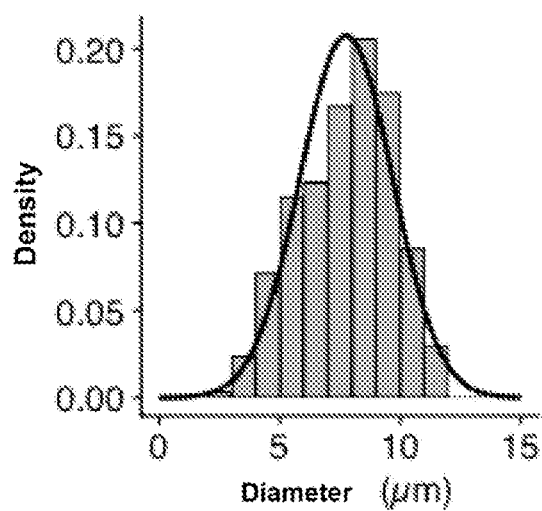
FIGS. 2A and 2B show the distribution of droplet size within emulsions A (FIG. 2A) and B (FIG. 2B). The samples have a diameter respectively equal to 8±20% μm and to 5.3±20% μm.
Figure 2B:
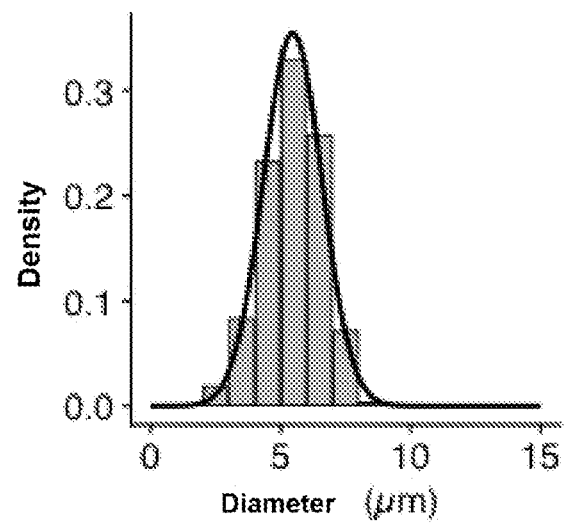

Soybean oil was dispersed and emulsified by hand in a continuous aqueous phase containing 15% by weight of sequenced copolymer surfactant Pluronic F-68 (CMC=0.03 g/l) and 1% by weight of sodium alginate at a final oil fraction equal to 75% by weight. The crude emulsion was subjected to shearing in a Couette cell device according to the method developed by Mason et al. [9] to fabricate two quasi-monodisperse emulsion samples with mean diameters of 8±2 μm (emulsion A, FIG. 2A) and 5.5±2 μm (emulsion B, FIG. 2B), respectively. For storage and handling, the emulsions were diluted to an oil fraction of 60% by weight with 1% by weight of Pluronic F-68 in the continuous phase and stored at 12° C. in a Peltier cabinet cooler for several weeks.

C) Preparation of the Functionalization Solutions

After evaporation of the chloroform in which the phospholipids are provided, the lipids are first dissolved in a polar solvent at a concentration of 1 mg/mL for DOPE-CF and 10 mg/mL for DSPE-PEG-biotin. Functionalization solutions were prepared with DMSO, acetonitrile, DMF, pyridine, butanone, ethyl acetate and triethylamine.

D) Functionalization Protocol of the Droplets with Phospholipids

The droplets in emulsion are diluted in a microtube to a concentration of approximately $5 \times 10^6$ droplets/μL dans 200 μL of a phosphate buffer (pH=7.2, 20 mM) supplemented with Tween 20 at CMC=0.006 g/L [10]. The suspension is centrifuged and rinsed 4 times with phosphate buffer to reduce the quantity of Pluronic F-68 in the continuous phase. After the last stage of rinsing, most of the aqueous solution is eliminated from the microtube to obtain 10 μL of emulsion. Next, 0 to 10% v/v of functionalization solution is added, and finally the phosphate buffer with Tween 20 (CMC) to reach a final volume of 200 μL of suspension.

The droplets are incubated for 90 minutes at ambient temperature in the presence of lipids in continuous phase, and are finally rinsed several times with the PB/Tween 20 CMC mixture to eliminate non-adsorbed phospholipids from the solution.

The quantity of phospholipids initially available in the continuous phase is adjusted by diluting the functionalization solution with its co-solvent so that the volume fraction of co-solvent is the same in all the experiments. For the most part, DMSO was used as co-solvent, at the volume fraction of 10% v/v.

The lipid concentration in the continuous phase is expressed in surface equivalents of the droplets relative to the number of molecules necessary to cover the droplet interface with a compact monolayer of lipids. The surface area per lipid head is 12 $nm^2$ for DSPE-PEG-biotin [11] and 0.5 $nm^2$ for DOPE-CF [12], which correspond, respectively, to a functionalization solution volume equal to 0.04 μL and 3.55 μL to reach a phospholipid surface equivalent for a suspension of droplets of 8 μm containing approximately $5 \times 10^6$ droplets.

E) Grafting Anti-Biotin IgGs onto Biotinylated Droplets

Coupling of the IgGs to the biotins present on the surface of the droplets was obtained after an incubation of the droplets for 30 minutes (200 μL, $5 \times 10^6$ droplets) with a variable quantity of a stock solution of mouse anti-biotin IgG conjugated to Alexa Fluor 488 (0.8 mg/mL) at ambient temperature in a phosphate buffer (PB, pH=7.2, 20 mM, Tween 20 at the CMC). For 8-μm droplets, the volume of stock solution to use to obtain a concentration corresponding to a surface equivalent of IgG on the droplets is equal to 2.5 μL if a molecular surface area of 120 $nm^2$ IgG is considered [13].

The droplets are rinsed several times in the same buffer to eliminate the unreacted IgGs and observed by microscopy.

F) Grafting of Streptavidin onto Biotinylated Droplets.

Streptavidins are specifically adsorbed on the surface of droplets functionalized by biotinylated lipids. Coupling was obtained after an incubation of the droplet suspension for 30 minutes (200 μL, $5 \times 10^6$ droplets) with a variable quantity of a stock solution of FluoProbes 488 streptavidin solution (1 mg/mL) at ambient temperature in a phosphate buffer (PB, pH=7.2, 20 mM, Tween 20 at the CMC). For 8-μm droplets, the volume of stock solution to use to obtain a concentration corresponding to a surface equivalent of streptavidin on the droplets is equal to 5.78 μL if a molecular surface area of 16.6 nm² per streptavidin is considered [13].

The droplets are rinsed several times in the same buffer to eliminate the unreacted streptavidin and observed by microscopy.

G) Microscopy and Image Analysis

The bright-field and fluorescent images were acquired by a Zeiss Axio Observer Z1 microscope (Oberkochen, Germany) connected to a PCO Edge 4.2 sCMOS camera (PCO, Germany). Epi-illumination was done with a Lumencor Spectra X LED system. The size and fluorescence distribution of the droplets in emulsion were measured by microscopy and image analysis. All the calculations were done with Fidji/ImageJ [5] and R [6] software. The droplets were observed with a Zeiss ×40 objective. The spinning disk microscopy recordings were done with a Leica SD AF microscope, with an ×40 objective.

H) Flow Cytometry

The droplets in emulsion were characterized with a BD Accuri C6 cytometer (BD Biosciences, New Jersey, USA).

I) Fabrication of the Microfluidic Device.

The device is made of PDMS using standard soft lithography techniques [14]. An SU-8 master (SU-8 20XX, Microchem) was fabricated on a silicon wafer using a direct laser writing masking device (Kloe Dilase 650), followed by PDMS molding (RTV 615, ratio 1:10 for the crosslinking agent, RTV 615, Momentive Performance Materials), followed by heat treatment at 80° C. for two hours. The PDMS surfaces and the cover glass (VWR, 50×24 mm) which closes the channel were treated with 02 plasma (Cute Plasma, Korea) before sealing the two parts of the chip together. The dimensions of the channel at the flow focusing junction are: width (w)=10 μm, height (h)=12 μm and length (l)=10 μm.

J) Ferrofluid Synthesis

The ferrofluid is made up of maghemite ($Fe_2O_3$) nanoparticles produced by co-precipitation in an aqueous phase of Fe (II) and Fe (III) under alkaline conditions, according to the method developed by Massart [15]. The nanoparticle size is comprised between 5 and 20 nm and depends on the reaction kinetics. For the experiments described below, particles with a size distribution of 7±1.6 nm were used. After synthesis, the aqueous phase is exchanged with chloroform by using an excess of oleic acid playing the role of surfactant and stabilizer. The iron concentration in the final product was characterized and is equal to 1.57 M.

Results

1. Droplet Fluorescence Distribution

Figure 2C:
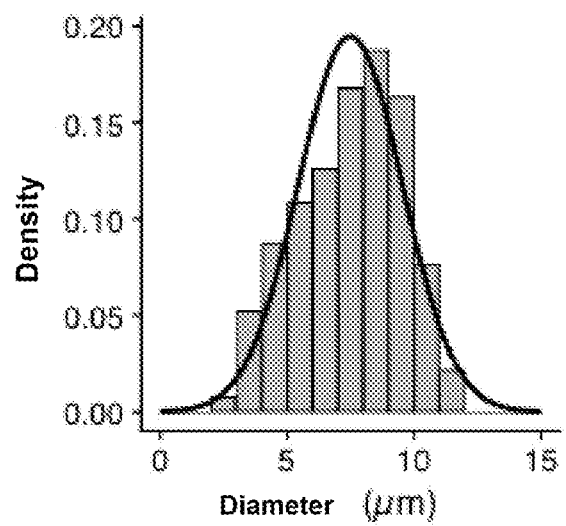
FIG. 2C is the size distribution of a sub-sample of diameter 8±1 μm (emulsion C).

A fluorescent phospholipid, DOPE carboxyfluorescein (CF), was dissolved in 10% v/v of DMSO in water according to the protocol described in the "Materials and Methods" part, section D), to study its insertion on the surface of the 8-μm soybean oil droplets. FIG. 3A shows a droplet image by spinning disk confocal microscopy. The droplets have a homogeneous fluorescent interface and a nearly black central portion, which indicates that the fluorescent phospholipids are only present on the surface (see also FIG. 3B). After measuring the fluorescence distribution of droplets with a bright-field epifluorescence microscope on several thousand objects, FIG. 3D shows the fluorescence distribution of an emulsion sub-sample (emulsion C, FIG. 2C) with a diameter of 8±1 μm. The fluorescence is very homogeneous and follows a normal distribution with a standard deviation of 9%.

2. Fluorescence Intensity as a Function of Droplet Size.

By using image analysis software on the droplet epifluorescence images, with the appropriate binary threshold, it is possible to represent the integrated fluorescence intensity over the entire planar area of the droplets $I_{Total}$. FIG. 3E thus shows that $I_{Total}$ varies linearly with the square of the droplet radius. Since fluorescence, supposed to be proportional to the quantity of lipids on the droplets, is only located at the emulsion surface, the mean fluorescence per object is expressed according to the following equation (Eq. 1):

$$\langle I \rangle = \frac{I_{Total}}{R^2}$$

and is proportional to the molecular density of lipid surface Γ per surface area unit.

3. Absorption Titration of DOPE-CF at the Droplet Surface.

To measure and characterize the adsorption equilibrium of model fluorescent phospholipids at the emulsion interface, 8-μm soybean oil droplets (emulsion C) were functionalized in an aqueous solution containing 10% v/v of DMSO and a DOPE-CF lipid concentration ranging from 0.1 to 20 surface equivalents, following the protocol summarized in the Materials and Methods part, section D). FIG. 4 shows the mean fluorescence intensity per droplet, which is directly linked to the surface lipid density, as a function of the lipid concentration. This is expressed by number of equivalents relative to the surface coverage by a lipid monolayer. The curve corresponds to a Langmuir isotherm verifying the following equation (Eq. 2):

$$\langle I \rangle = \langle I_0 \rangle \frac{1}{1 + \frac{1}{KC}}$$

where $\langle I_0 \rangle$ is the mean maximum intensity value, C is the lipid concentration expressed in equivalents and K is the apparent affinity constant. According to the results obtained, the affinity constant between DOPE-CF and the droplets is equal to $K_{DOPE-CF}=0.6\pm0.25$ eq$^{-1}$.

4. Titration of the Adsorption of Biotinylated Lipids on the Droplet Surface

The inventors have shown in the past that the emulsion droplets can be functionalized with adhesive proteins such as streptavidin [2] or immunoglobulins [4]. This is usually done by first inserting DSPE-PEG-biotin molecules at the oil/water interface onto which anti-biotin IgGs or streptavidin are grafted in a specific way.

8-μm soybean oil droplets were suspended in a PB/Tween 20 CMC buffer containing 10% v/v of DMSO and an initial DSPE-PEG-biotin concentration ranging from 0 to 200 surface equivalents. After 90 minutes of incubation at ambient temperature, the droplets are rinsed according to the protocol indicated in the Materials and Methods part, section D).

To show the presence of nonfluorescent DSPE-PEG-biotin and construct the titration curve, a saturating quantity of fluorescent anti-biotin IgG is added to the suspension (5 surface equivalents). After 30 minutes of incubation, the droplets are rinsed (Materials and Methods, section F) and their fluorescence is quantified by microscopy. FIG. 5 shows that the titration curve, represented by the fluorescence density relative to the biotinylated lipid concentration, follows a Langmuir isotherm with an apparent equilibrium constant $K_{DSPE-PEG-biotin}=0.03\pm0.015$ eq$^{-1}$.

5. Fluorescence Distribution of Biotinylated Droplets onto which Proteins are Grafted.

8-μm droplets are biotinylated by incubation with 100 eq. of DSPE-PEG-biotin and 10% v/v of DMSO in the continuous phase. They are then incubated with 5 equivalents of streptavidin or 10 equivalents of anti-biotin IgGs. The normalized fluorescence histograms obtained are shown in FIGS. 6A (DSPE-PEG-biotin-streptavidin) and 6B (DSPE-PEG-biotin-IgG). The CV equals 14% and 16%, respectively.

6. Titration of Protein Grafting onto Biotinylated Droplets.

Knowing the apparent association constant for DSPE-PEG-biotin, the titration curves related to the specific grafting of streptavidin and anti-biotin IgGs to biotinylated droplets were determined. First, the soybean oil droplets (8 μm, emulsion C) are biotinylated using a PB/Tween 20 CMC buffer solution containing 10% v/v of DMSO and containing 100 equivalents of DSPE-PEG-biotin, concentration 3 times greater than that corresponding to the association constant of these biotinylated lipids. The droplets are incubated for 30 minutes (which is much longer than the time necessary to reach equilibrium in view of the kinetic studies conducted and reported in FIGS. 8A and 8B), in solutions of streptavidin and IgG with concentrations respectively ranging from 0 to 5 and 0 to 20 protein surface equivalents. FIGS. 7A and 7B show that the quantity of protein on the surface saturates above 1 eq. of streptavidin and 10 eq. of IgG respectively. By using the Langmuir isotherm as adjustment equation, the following apparent affinity constants of the proteins to the biotinylated droplets are determined. $K_{Streptavidin}=6.9\pm2.3$ eq$^{-1}$ and $K_{IgG}=0.5\pm0.18$ eq$^{-1}$.

7. Influence of the Nature and the Concentration of the Surfactant

As detailed in the Materials and Methods part, section D), the fabrication of functionalized droplets involves two surfactants (Pluronic F-68) being used for the emulsification step, while the second (Tween 20) is used in the functionalization step. Before functionalization, Pluronic F-68 is usually eliminated to reach a concentration below its CMC. To study the influence of the presence of surfactants during the biotinylation step, the mean fluorescence intensity was measured for droplets grafted with IgG, for which the types and concentrations of surfactants in the presence of DSPE-PEG-biotin during the functionalization step were varied. Table 1 below shows the mean fluorescence and the standard deviation measured for droplets coated with IgGs, which were previously functionalized by DSPE-PEG-biotin in the absence of surfactant in the phospholipid solution (sample 1), in the presence of Pluronic F-68 or Tween 20 at concentrations equal to their respective CMC (samples 2 and 4) or much higher than their CMC (samples 3 and 5). After incubation and rinsing, the IgG grafting step was performed in all cases with a PB/Tween 20 CMC buffer.

| Sample | Surfactant | Mean | Fluorescence concentration (relative to sample 3) | Standard deviation | CV (%) |
|---|---|---|---|---|---|
| 1 | none | — | 13.90 | 2.47 | 17.8% |
| 2 | Pluronic F-68 | CMC | 13.15 | 2.58 | 19.6% |
| 3 | Pluronic F-68 | 15xCMC | 1.00 | 0.09 | 9.1% |
| 4 | Tween 20 | CMC | 14.81 | 2.48 | 16.8% |
| 5 | Tween 20 | 10xCMC | 2.86 | 0.56 | 19.5% |

-continued

The results obtained show that the presence of a surfactant at high concentration, whether Pluronic F-68 or Tween 20, is detrimental to functionalizing the droplet interface droplets with biotinylated lipids. In return, for low surfactant concentrations, the fluorescence intensities are maximized, do not depend on the nature of the surfactant used and are similar to those measured in the absence of surfactant (PB alone).

8. Influence of the Nature of the Co-Solvent on Lipid Adsorption.

To study the influence of the co-solvent nature on the adsorption of lipids on the droplet surface, several usual polar aprotic solvents have been used to prepare the functionalization solutions: ethyl acetate, pyridine, butanone, DMF, acetonitrile, triethylamine and DMSO. All the experiments were performed by diluting DOPE-CF or DSPE-PEG-biotin in pure co-solvent, then by working with a volume fraction of co-solvent of 10% v/v in the functionalization mixture. Except for triethylamine, whose presence leads rapidly to destabilization of the emulsion, all the other co-solvents have no visible influence on the droplet stability during incubation at ambient temperature. The lipid concentrations were chosen at 2.5 eq. for DOPE-CF and 10 eq. for DSPE-PEG-biotin, respectively. Fluorescent IgGs were used at 5 eq. to reveal the presence of biotinylated lipid. FIGS. 9A and 9B show that for both lipids considered, the use of a polar aprotic co-solvent leads to a significant increase in lipid adsorption, and this increase depends slightly on the value of the co-solvent dipole moment.

9. Influence of the DMSO Concentration on Lipid Adsorption.

For the particular case of DMSO used as co-solvent, the effect of the increase of its volume fraction in the continuous phase on lipid adsorption (DOPE-CF, 2.5 eq.) at the droplet surface (8 μm) was evaluated. FIG. 10 shows that the total fluorescence of droplets functionalized by DOPE-CF measured by flow cytometry, increases with the volume fraction of DMSO and saturates above 10% v/v of co-solvent in the continuous phase.

10. Preparation of a Magnetic Emulsion

An emulsion comprising droplets functionalized by IgGs and comprising a magnetic core was prepared by using a dispersed phase composed of a ferrofluid of $Fe_2O_3$ nanoparticles suspended in mineral oil.

Since chloroform is very volatile, the nanoparticles are redispersed in a non-volatile hydrophobic phase that will be further emulsified. After having visually examined several different oils (vegetable, mineral, silicone), different concentrations of nanoparticles and oleic acid, an optimal formulation for a ferrofluid stable over time was determined, composed of mineral oil, 10% v/v initial ferrofluid (1.57 M) and 5% v/v oleic acid.

The magnetic droplets were then produced using a pressure controlled microfluidic flow focusing device having channels with rectangular cross section equal to 10×12 μm, shown in FIG. 11. After emulsification, the droplets are functionalized with biotinylated phospholipids and fluorescent IgGs according to the protocols described in the Materials and Methods part, sections D) and E). The fluorescence homogeneity within the sample is very high (FIG. 13A), with a CV near 10% as shown in FIG. 12B. When a static magnetic field is applied using a commercial permanent magnet, the droplets align (FIG. 13B) due to the superparamagnetic nature of their core, which is the expected behavior for such objects.

11. Flow Cytometry: FL-SSC Diagram

A density diagram showing fluorescence (FL) as a function of side scatter channel (SSC) was plotted for droplets functionalized by DSPE-PEG-biotin, onto which fluorescent IgGs are then grafted according to the protocols described in the Materials and Methods part, sections D) and E).

It is observed (FIG. 14A) that for a given SSC value, the fluorescence range measured is narrow.

Comparative Results

12. Preparation of Functionalized Droplets According to a Protocol of the Prior Art For comparative purposes, emulsion droplets were prepared by using a protocol described in the prior art [4], during which lipids are introduced into the oil before emulsification:

A solution of DSPE-PEG-biotin in chloroform was prepared, and the necessary quantity to reach a lipid concentration of 0.05 mg/mL was added into the soybean oil. After evaporation of the chloroform from the oil by heating and sonication, monodispersed droplets were generated with the Couette device, then fluorescent anti-biotin IgGs were grafted on their surface.

13. Flow Cytometry: FL-SSC Diagram

A density diagram showing fluorescence (FL) as a function of side scatter channel (SSC) was plotted for droplets functionalized according to the protocol described in the prior art (see section 12).

It is observed (FIG. 14B) that the optical fluorescent signal is much more scattered than the one obtained by functionalizing the droplets according to the method of the invention.

14. Droplet Fluorescence Distribution

The comparison of the images obtained by wide-field epifluorescence microscopy for droplets functionalized according to the protocol of the prior art (FIG. 15A) with droplets functionalized according to the method of the invention (FIG. 3C) shows that this method leads to a greater functionalization homogeneity.

This is confirmed by the fluorescence histogram of droplets functionalized according to the protocol of the prior art (FIG. 15B), which follows a log-normal distribution, with a factor of approximately ten between the least fluorescent and most fluorescent droplet.

For comparison, the fluorescence distribution obtained with the method of the invention is narrower and follows a normal distribution, with a CV still below 20% (FIG. 6B).

Application to the Study of Phagocytosis of Halogenated Functionalized Emulsion Droplets Step 1: Cell Preparation RAW 264.7 murine macrophages purchased from ECACC are cultured in untreated T-80 flasks (VWR) filled with DMEM 4.5 g/L L-glucose supplemented with 10% v/v fetal bovine serum and 1% Penicillin-Streptomycin, in an incubator at 37° C. and 5% $CO_2$. 24 hours before the experiment, they are detached with TryPLE and mechanical stirring, and inoculated in optical glass bottom Petri dishes (Fluorodish F35-100, WPI) in an amount of $10^6$ cells per cover glass. A schematic representation of these Petri dishes is shown in FIG. 16A.

Step 2: Target Preparation

Halogenated vegetable oil droplets, denser than the aqueous continuous phase, were used.

2.1: Oil Droplet Preparation

DSPE-PEG2000-biotin biotinylated phospholipids are dissolved in soybean oil at 0.05 mg/mL. The aqueous phase of the emulsion is made up of 15% w/w of F-68, and 0.5-2% w/w sodium alginate depending on the desired droplet size. Halogenated oil is added dropwise into the aqueous phase with gentle stirring with a spatula to obtain a coarse emulsion, up to 75% oil by mass. This emulsion is then sheared in a Couette rheometer at 5000 $s^{-1}$, which reduces the droplet size distribution. The sheared emulsion is then diluted in order to reach a mass fraction of oil of 5% and F-68 of 1%. This suspension is decanted several times with a 1% F-68 solution in order to eliminate residual small droplets.

2.2: Target Functionalization

It was decided to use $2 \times 10^6$ targets/cover glass.

The targets are washed and centrifuged 3 times with a 0.007% Tween 20 phosphate buffer. They are then incubated with Alexa 488 anti-biotin antibodies, in the amount of 1 antibody to 1 DSPE-PEG2000-biotin present on the droplet surface for 45 minutes at ambient temperature. They are then washed 3 times again with 0.007% Tween 20 phosphate buffer before return to a final suspension of $2 \times 10^5$ targets/μL.

Step 3: Contacting the Targets and Cells

Immediately before contacting, for each cover glass of cells, 10 μL of targets at the concentration of $2 \times 10^5$ targets/μL are suspended in 30 μL of DMEM 4.5 g/L L-glucose without phenol red at 37° C. The cover glasses of inoculated cells are rinsed 24 h later with 1 mL of DMEM 4.5 g/L L-glucose with no phenol red at 37° C.

The target suspension is injected into the chamber. The chambers are left to incubate at 37° C. and 5% $CO_2$ for 45 minutes. In the case of oil droplets, the cover glass inoculated with cells must be on top, so that the less dense droplets rise on contact with them. Conversely, in the case of polystyrene beads, the inoculated cover glasses must be at the bottom so that the beads sediment on contact with them.

After 45 minutes, the chambers are rinsed with PBS so as to eliminate all the droplets that have not been internalized, and fixed with a 4% paraformaldehyde solution for 20 minutes at ambient temperature.

Step 4: Fixation

The cover glasses are first incubated with 50 mM of $NH_4Cl$ for 2 minutes, then permeabilized with 0.1% v/v Triton X-100 for 10 minutes, and saturated with a 4% w/w bovine serum albumin. They are incubated with 1 μg/cover glass of rat anti-mouse CD16/CD32 antibodies for 15 minutes, then rinsed with 4% BSA solution.

Step 5: Observation

The fixed samples are observed under a Leica TCS SP8 confocal microscope, with a 40× oil immersion objective, and the image is taken by two Leica hybrid detectors. Lasers at 405, 488, 552 and 638 nm illuminate the fluorophores present. The light emitted by the sample is not filtered, but rather separated by a prism. The wavelength windows collected are determined on a case-by-case basis depending on the fluorophores present in order to minimize interference between signals.

FIGS. 16B and 16C show two images representative of the emulsion droplet phagocytosis experiments whose functionalization protocol is described above. The droplets are functionalized by biotinylated lipids (FIG. 16B) then by anti-biotin antibodies (FIG. 16C) recognized by macrophage receptors involved in phagocytosis. The number of droplets internalized is greater in FIG. 16C than in FIG. 16B, which is the control experiment.

REFERENCES

[1] L.-L. Pontani, I. Jorjadze, V. Viasnoff, J. Brujic, Proc. Natl. Acad. Sci. U.S.A 109 (2012) 9839.
[2] J. Fattaccioli, J. Baudry, N. Henry, F. Brochard-Wyart, J. Bibette, Soft Matter 4 (2008) 2434.
[3] N. Bourouina, J. Husson, F. Waharte, R. B. Pansu, N. Henry, Soft Matter 7 (2011) 9130.
[4] K. Ben M'Barek, D. Molino, S. Quignard, M. Plamont, Y. Chen, P. Chavrier, J. Fattaccioli, Biomaterials 51 (2015) 270.
[5] M. Hadorn, E. Boenzli, K. T. Sørensen, H. Fellermann, P. Eggenberger Hotz, M. M. Hanczyc, P. Eggenberger, M. M. Hanczyc, P. Eggenberger Hotz, Proc. Natl. Acad. Sci. U.S.A. 109 (2012) 20320.
[6] L. Feng, L.-L. Pontani, R. Dreyfus, P. Chaikin, J. Brujic, Soft Matter 9 (2013) 9816.
[7] A. R. Thiam, N. Bremond, J. Bibette, Langmuir 28 (2012) 6291.
[8] O. Campàs, T. Mammoto, S. Hasso, R. a Sperling, D. O'Connell, A. G. Bischof, R. Maas, D. a Weitz, L. Mahadevan, D. E. Ingber, Nat. Methods 11 (2013) 183.
[9] T. Mason, J. Bibette, Phys. Rev. Lett. 77 (1996) 3481.
[10] K. L. Mittal, J. Pharm. Sci. 61 (1972) 1334.
[11] N. V. Efremova, B. Bondurant, D. F. O'Brien, D. Leckband, Biochemistry 39 (2000) 3441.
[12] D. S. Banks, C. Fradin, Biophys. J. 89 (2005) 2960.
[13] T. C. Werner, J. R. Bunting, R. E. Cathou, Proc. Natl. Acad. Sci. U.S.A 69 (1972) 795.
[14] Y. Xia, G. M. Whitesides, Angew. Chemie Int. Ed. 37 (1998) 550.
[15] R. Massart, IEEE Trans. Magn. 17 (1981) 1247.

The invention claimed is:

1. A method for obtaining a colloid comprising functionalized liquid colloidal particles comprising the following steps:
   a) dispersing an oil in an aqueous solution comprising a fragmentation surfactant, leading to obtaining an emulsion comprising oil droplets suspended in an aqueous phase;
   b) dissolving lipids aimed at functionalizing the oil droplets in a polar aprotic solvent, leading to obtaining a functionalization solution;
   c) preparing a functionalization mixture comprising the emulsion and the functionalization solution, the volume fraction of the polar aprotic solvent in the functionalization mixture being comprised between 1 and 15%;
   d) incubating the functionalization mixture, during which at least a part of the lipids initially present in the functionalization solution are adsorbed on the surface of the oil droplets initially present in the emulsion; and
   e) eliminating non-adsorbed lipids during step d);
   thus allowing to obtain a colloid comprising functionalized liquid colloidal particles consisting of the oil droplets obtained after step a) on the surface of which the lipids are adsorbed during step d).

2. The method according to claim 1, wherein the polar aprotic solvent is selected from the group consisting of dimethyl sulfoxide (DMSO), ethyl acetate, acetonitrile, pyridine, butanone, triethylamine, N,N-dimethylformamide (DMF), and mixtures thereof.

3. The method according to claim 1, wherein the oil dispersed in aqueous solution during step a) is a mineral oil, a vegetable oil, a silicon oil, a halogenated oil, or a mixture thereof.

4. The method according to claim 1, wherein the lipids comprise at least one fluorophore group and/or at least one biomolecule optionally grafted via a linker.

5. The method according to claim 1, wherein the lipids are phospholipids optionally grafted with at least one fluorophore group and/or at least one biomolecule, optionally via a linker.

6. The method according to claim 1, wherein in step c), a dispersion surfactant is added.

7. The method according to claim 1, wherein in step c), a buffer solution with a pH comprised between 5 and 9 is added.

8. The method according to claim 1, wherein incubation step d) is performed at a temperature between 15° C. and 40° C. and for a duration between 10 min and 10 h.

9. The method according to claim 1, wherein the oil dispersed in the aqueous solution comprises $Fe_2O_3$ nanoparticles in suspension, thus allowing to obtain a colloid comprising magnetic functionalized liquid colloidal particles.

10. The method according to claim 1, wherein it comprises, after step e), an additional step f) of grafting biomolecules onto the lipids.

11. The method according to claim 1, wherein in step c), the volume fraction of the polar aprotic solvent in the functionalization mixture is comprised between 8 and 15%.

12. The method according to claim 1, wherein the polar aprotic solvent is dimethyl sulfoxide (DMSO).

13. The method according to claim 5, wherein the phospholipids are phosphatidylethanolamines, optionally grafted with at least one fluorophore group and/or at least one biomolecule, optionally via a linker.

14. The method according to claim 5, wherein the phospholipids are selected from the group consisting of 1,2-dioleoyl-sn-glycero-3-phosphoethanolamine carboxyfluorescein (DOPE-CF), 1,2-distearoyl-sn-glycero-3-phosphoethanolamine-polyethylene glycol biotin (DSPE-PEG-biotin), and mixtures thereof.

15. A colloid comprising functionalized liquid colloidal particles obtainable by the method according to claim 1.

* * * * *